United States Patent [19]

Foguet et al.

[11] Patent Number: 4,719,225

[45] Date of Patent: Jan. 12, 1988

[54] THIOPHENE RING-SUBSTITUTED α-(ALKYLAMINOPROPIONYL)-THIOPHENES AND THE METHOD FOR PREPARING THE SAME

[75] Inventors: Rafael Foguet; Ernesto Forne; Aurelio Sacristan; Jose A. Ortiz, all of Barcelona, Spain

[73] Assignee: Ferrer Internacional S.A., Barcelona, Spain

[21] Appl. No.: 936,706

[22] Filed: Dec. 1, 1986

Related U.S. Application Data

[63] Continuation-in-part of Ser. No. 840,651, Mar. 17, 1986, abandoned.

[30] Foreign Application Priority Data

Mar. 20, 1985 [ES] Spain ........................................ 541911

[51] Int. Cl.⁴ ..................... A61K 31/38; C07D 333/22
[52] U.S. Cl. ........................................ 514/448; 549/72
[58] Field of Search ........................... 549/72; 514/448

[56] References Cited

U.S. PATENT DOCUMENTS 3,193,551  7/1965  Passedouet et al. ................. 549/72
3,372,162  3/1968  Pesson et al. ....................... 549/72
3,505,338  4/1970  Wright et al. ....................... 549/72

Primary Examiner—Alan Siegel
Attorney, Agent, or Firm—Michael J. Striker

[57] ABSTRACT

The invention is concerned with the novel thiophene ring-substituted α-(alkylaminopropionyl)-thiophenes represented by the formula (I),

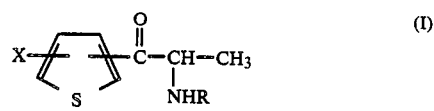

or a pharmaceutically-acceptable salt thereof, a process for the preparation of them, and a pharmaceutical composition which contains these new compounds as active ingredient and can be used as antidepressant agents.

11 Claims, No Drawings

THIOPHENE RING-SUBSTITUTED α-(ALKYLAMINOPROPIONYL)-THIOPHENES AND THE METHOD FOR PREPARING THE SAME

This application is a continuation-in-part of Ser. No. 840,651 filed 3/17/86, now abandoned.

BACKGROUND OF THE INVENTION

The present invention relates to novel thiophene ring-substituted α-(alkylaminopropionyl)-thiophenes which have an effective antidepressant activity, its pharmacologically-acceptable salts, and process for preparing the same.

More particularly, the present invention relates to novel α-(alkylaminopropionyl)-thiophenes represented by the general formula (I),

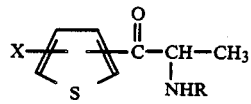

wherein X is a group different from hydrogen selected between methyl or chlorine and R is an alkyl-linear or branched chain-group having 3 to 4 carbon atoms, its pharmacologically-acceptable salts and process for preparing the same.

FIELD OF THE INVENTION

The thiophene ring non-substituted derivatives of α-(alkylaminopropionyl)-thiophene are known in the literature. Therefore, French Pat. No. 3414M discloses α-(alkylaminopropionyl)-thiophenes showing anorexic activity which is devoid of central excitatory action or cardiovascular action, and British Pat. No. 1,313,150 discloses, among other compounds, α-(alkylaminopropionyl)-thiophenes showing neuroleptic, tranquilizing and analgesic action.

SUMMARY OF THE INVENTION

The inventors have found out that the compounds of this invention, which differ from the compounds in the aforesaid patents as regards to the presence of a X substituent different from hydrogn, have moreover a pharmacological activity quite different from that mentioned in the aforesaid patents. As a matter of fact the thiophene ring-substituted α-(alkylaminopropionyl)thiophenes of general formula (I) have an effective antidepressant activity as evidenced by R. D. Prosolt's test (Immobility behavioural despair test in mice: Arch. Int. Pharmacodyn., 229, 327–336, 1977). Consequently, the compounds of this invention are useful as a medicament for treating depressions.

The present invention is based on this finding.

DETAILED DESCRIPTION OF THE INVENTION

Pharmacologically-acceptable salts of the compounds having the said formula (I) are acid addition salts. Acid addition salts include mineral acid salts such as hydrochloride, sulfate, nitrate, hydrobromide, hydroiodide, phosphate, etc.; or organic acid salts such as acetate, maleate, fumarate, citrate or tartarate, etc.

Non-limitative examples of the compounds of this invention include:

(1) 2-[α-(sec-butylaminopropionyl)]-4-chlorothiophene and HCl
(2) 2-[α-(sec-butylaminopropionyl)]-4-methylthiophene and HCl
(3) 2-[α-(n-propylaminopropionyl)]-4-methylthiophene and HCl
(4) 2-[α-(iso-propylaminopropionyl)]-5-chlorothiophene and HCl
(5) 2-[α-(n-propylaminopropionyl)]-5-chlorothiophene and HCl
(6) 2-[α-(sec-butylaminopropionyl)]-5-chlorothiophene and HCl
(7) 4-[α-(iso-propylaminopropionyl)]-2-chlorothiophene and HCl
(8) 4-[α-(sec-butylaminopropionyl)]-2-chlorothiophene and HCl According to the present invention the novel compounds, thiophene ring-substituted α-(alkylaminopropionyl)-thiophenes, represented by the general formula (I), can be prepared by the following method:

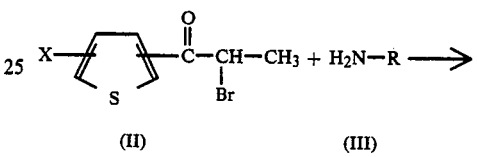

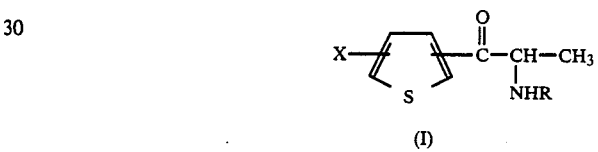

Bromine displacement in the compounds of formula (II), wherein X is as defined above for (I), by the amines of formula (III), wherein R is as defined above for (I), occurs in an inert medium, preferably acetonitrile, and at a maximal temperature of 50° C., followed by vacuum evaporation of solvent, removal and evaporation to dryness of extracts. From the residue thus obtained, corresponding to the compounds of formula (I), it is possible to form their pharmaceutically acceptable salts, preferably hydrochlorides, by treating the respective acids in an inert solvent; ethers, specially diethyl ether, are preferred. Then the formed precipitate is separated by filtration.

α-(Bromopropionyl)-thiophene precursors of general formula (II) are obtained by conventional methods in Organic Chemistry; the reaction of propionyl-thiophenes with bromine in a medium composed by an aliphatic-chlorinated hydrocarbon, for example, methylene chloride, chloroform or carbon tetrachloride, are preferred. In turn, propionyl-thiophenes are susceptible to be obtained either by acylation of respective thiophenes with a derivative of propionic acid, preferably propionyl chloride, under suitable conditions of Friedel-Crafts' reaction, or by reacting lithium derivatives of respective thiophenes with propionitrile. When X is chlorine, starting compounds such as commercially-available chlorothiophenes or dichlorothiophenes are, if possible, used and the substituent X=Cl may be introduced into the synthesis sequence on intermediate steps depending on the desired position. Sulphuryl chloride is preferred as a chlorinating agent. When X is methyl, respective methylthiophenes are, if possible, also used.

The preparation of α-(bromopropionyl)-thiophene precursors of formula (II) is hereinafter illustrated.

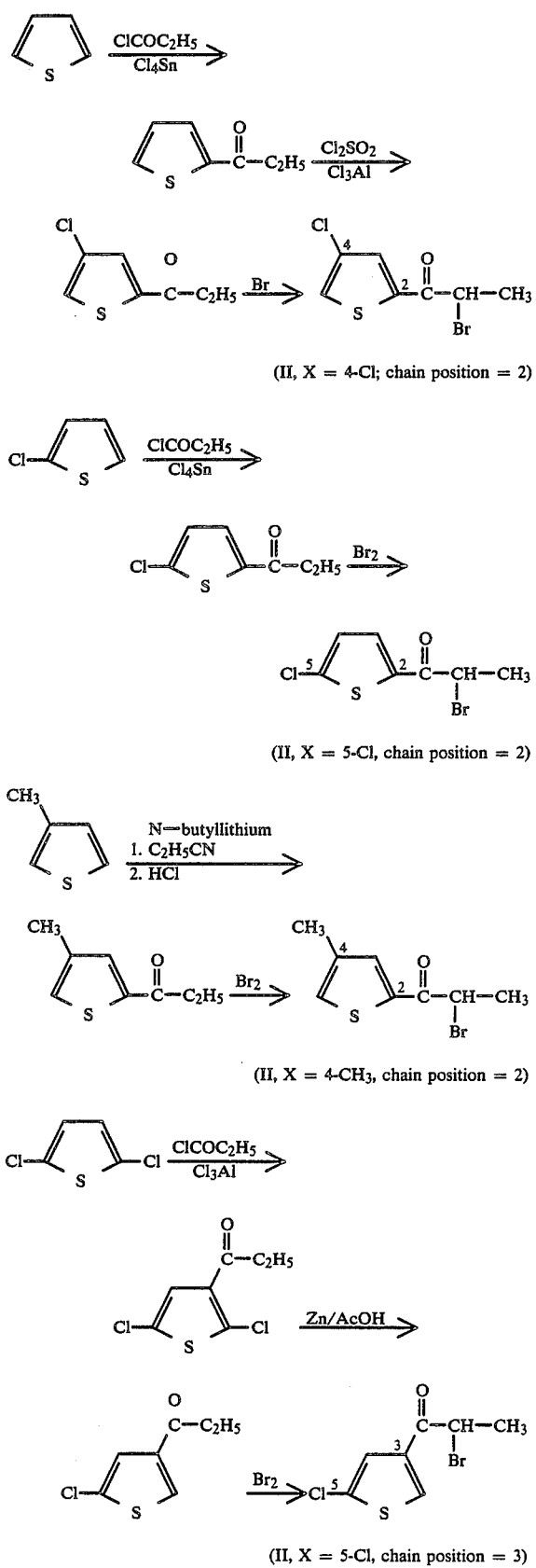

ANTIDEPRESSANT ACTIVITY

The compounds of the present invention have an effective antidepressant activity as evidenced by the R. D. Porsolt's test (Immobility behavioural despair test in mice: Arch. Int. Pharmacodyn., 229, 327–336, 1977).

By considering such a property, the compounds of this invention are useful agents for treating depression.

The compounds of the present invention mixed with pharmaceutically acceptable carriers can be administered by the oral route in the form of tablets, capsules, coated tablets, syrups, solutions, etc., by injectable route and by rectal route at daily doses ranging from 2.5 to 250 mg/kg.

The novel features which are considered characteristic of the invention are set forth in particular in the appended claims. The invention itself, however both as to its construction and its method of operation, together with additional objects and advantages thereof, will be best understood from the following description of specific embodiments.

EXAMPLE 1

2-[α-(sec-butylaminopropionyl)]-4-chlorothiophene hydrochloride

To 26.05 g of α-bromo-4-chloro-2-propionylthiophene—prepared according to Spanish Pat. No. 541.911—in 30 ml of acetonitrile, 18.8 g of sec-butylamine are slowly added without exceeding 32° C. As the exothermia diminishes, the mixture is left under stirring at room temperature. The solvent is evaporated at vacuum (below 35° C.), taken in methylene chloride (150 ml) and water (150 ml); the aqueous phase is removed with methylene chloride, the organic extracts are washed with water, dried and evaporated to dryness. The crude product (21.2 g) is dissolved in 400 ml of dry ethyl ether, cooled with water-ice bath and a dry HCl (g) stream is passed through; the insolubilized hydrochloride (20.0 g) is recrystallized from isopropanol to give 9.5 g (32%) of a white solid, m.p. 208°–209° C. and analysis correct.

IR Spectrum (KBr) cm$^{-1}$: 3200–2440, 1670, 1550, 1400, 1230, 1110, 1090, 860.

$^1$H—NMR (d$_6$—DMSO+D$_2$O) ppm: 0.87 (t, 3H, J=7 Hz; CH$_3$—), 1.14 (d, 5H, J=6 Hz; CH$_3$—CH—NH—), 1.47 (d +wide band, 5H, J=7 Hz; $\overline{CH_3}$— and —CH$_2$—), 2.87 (m, 1H; >CH—NH—), 4.48 (m, 1H; >$\overline{CH}$—CH$_3$), 8.11 (s, 1H; H-thiophene) and 8.26 (s, 1H; H-thiophene).

EXAMPLE 2

2-[α-(sec-butylaminopropionyl)]-4-methylthiophene hydrochloride

From 33.9 g of α-bromo-4-methyl-2-propionylthiophene—prepared according to Spanish Pat. No. 552.220—26.6 g of sec-butylamine in 45 ml of acetonitrile, and operating as described in Ex. 1, 41.9 g of crude product are isolated, respective hydrochloride (23.1 g) formed in ethyl ether is recrystallized in absolute ethanol to give 12.4 g (32%) of a white solid, m.p. 227°–229° C. and analysis correct.

IR Spectrum (KBr) cm$^{-1}$; 3200–2400, 1665, 1545, 1410, 1225, 1100, 885, 860.

$^1$H—NMR Spectrum (d$_6$—DMSO) ppm: 0.90 (t, 3H, J=7 Hz; CH$_3$—), 1.25 (d, 3H, J=7 Hz; CH$_3$—CN NH—), 1.57 (d+wide band, 5H, J=7 Hz; $\overline{CH_3}$— and CH$_2$—), 2.26 (s, 3H; CH$_3$-thiophene), 3.00 (m, 1H;

>CH—NH—), 5.10 (m, 1H; >CH—CH$_3$), 7.80 (s, 1H; H-thiophene) and 8.20 (s, 1H; H-thiophene).

EXAMPLE 3

2-[α-(n-propylaminopropionyl)]-4-methylthiophene hydrochloride

From 33.9 g of α-bromo-4-methyl-2-propionylthiophene in 45 ml of acetonitrile and 21.5 g of n-propylamine, and operating as described in Ex. 1, 42.1 g of crude product are isolated, respective hydrochloride (26.1 g) formed in ethyl ether is recrystallized in acetonitrile-isopropanol (1:1) to give 11.8 g (33%) of a white solid, m.p. 211.3°-212° C. and analysis correct.

IR Spectrum (KBr) cm$^{-1}$: 3200–2400, 1660, 1410, 1230, 1215, 1105, 920, 780.

$^1$H—NMR (d$_6$—DMSO) ppm: 0.90 (t, 3H, J=7 Hz; CH$_3$—), 1.56 (d, 3H, J=7 Hz; CH$_3$—CH—CO—), 1.74 (m, 2H, J=8 Hz; —CH$_2$—), 2.27 (s, 3H; CH$_3$-thiophene), 2.82 (m, 2H, J=8 Hz; —CH$_2$—NH—), 5.00 (q, 1H, J=7 Hz; >CH—CO—), 7.81 (s, 1H; H-thiophene) and 8.07 (s, 1H; H-thiophene).

EXAMPLE 4

2-[α-(isopropylaminopropionyl)]-5-chlorothiophene hydrochloride

From 32.0 g of α-bromo-5-chloro-2-propionylthiophene—prepared as described in Spanish Pat. No. 541.911—in 40 ml of acetonitrile and 18.62 g of isopropylamine, and operating as described in Ex. 1, 30 g of crude product are isolated, respective hydrochloride (28.7 g) formed in ethyl ether is recrystallized from isopropanol to give 13.5 g (39%) of a white solid, m.p. 222.2°-223° C. and analysis correct.

IR Spectrum (KBr) cm$^{-1}$: 3160–2400, 1660, 1555, 1410, 1320, 1240, 1075, 1010, 825.

$^1$H—NMR (d$_6$—DMSO) ppm: 1.30 (d, 6H, J=6 Hz; —CH(CH$_3$)$_2$), 1.57 (d, 3H, J=7 Hz; CH$_3$—), 3.37 (m, 1H; CH(CH$_3$)$_2$), 5.17 (m, 1H; —CO—CH—), 7.42 (d, 1H, J=4 Hz; H-thiophene) and 8.37 (d, 1H, J=4 Hz, H-thiophene).

EXAMPLE 5

2-[α-(n-propylaminopropionyl)]-5-chlorothiophene hydrochloride

From 35.7 g of α-bromo-5-chloro-2-propionylthiophene in 45 ml of acetonitrile and 20.9 g of n-propylamine, and operating as described in Ex. 1, 31 g of crude product are isolated, respective hydrochloride (12 g) is recrystallized from isopropanol to give 7.73 g (20%) of a white solid, m.p. 190°-190.3° C. and analysis correct.

IR Spectrum (KBr) cm$^{-1}$: 3180–2400, 1665, 1410, 1320, 1230, 1010, 815, 720.

$^1$H—NMR Spectrum (D$_2$O) ppm: 1.00 (t, 3H, J=7.5 Hz; CH$_3$—), 1.68 (d, 3H, J=7 Hz; CH$_3$—CH—CO—), 1.82 (m, 2H; —CH$_2$—), 3.10 (m, 2H; —CH$_2$—N>), 5.00 (q, 1H, J=7.0 Hz; >CH—CO—), 7.25 (d, 1H, J=4 Hz, H-thiophene) and 7.94 (d, 1H, J=4 Hz; H-thiophene).

EXAMPLE 6

2-[α-(sec-butylaminopropionyl)]-5-chlorothiophene hydrochloride

From 32.9 g of α-bromo-5-chloro-2-propionylthiophene in 40 ml of acetonitrile and 23.8 g of sec-butylamine, and operating as described in Ex. 1, 28.4 g of crude product are isolated, respective hydrochloride (20.5 g) is recrystallized from isopropanol to give 9.2 g (26%) of a white solid, m.p. 191.3°-192° C. and analysis correct.

IR Spectrum (KBr) cm$^{-1}$: 3120–2400, 1660, 1550, 1420, 1235, 1010, 820.

$^1$H—NMR (d$_6$—DMSO+D$_2$O) ppm: 0.90 (2t, 3H, J=7 Hz; CH$_3$—), 1.27 (d, 3H, J=7 Hz; CH$_3$—CH—NH—), 1.59 (d+wide band, 5H, J=7 Hz; CH$_3$— and —CH$_2$—), 3.05 (m, 1H; >CH—NH), 5.15 (qt, 1H, J=7 Hz; >CH—CO—), 7.40 (d, 1H, J=4 Hz; H-thiophene) and 8.32 (d, 1H, J=4 Hz; H-thiophene).

EXAMPLE 7

4-[α-(isopropylaminopropionyl)]-2-chlorothiophene hydrochloride

From 33.9 g of α-bromo-2-chloro-4-propionylthiophene—prepared according to Spanish Pat. No. 541.911—in 40 ml of acetonitrile and 19.8 g of isopropylamine, and operating as described in Ex. 1, 31.0 g of crude product are isolated, respective hydrochloride (28.5 g) formed in ethyl ether is recrystallized in ethanol to give 9.3 g (30%) of a white solid, m.p. 244°-245° C. and analysis correct.

IR Spectrum (KBr) cm$^{-1}$: 3200–2420, 1670, 1550, 1455, 1420, 1210, 1190, 1170, 1100, 1000, 830.

$^1$H—NMR (D$_2$O) ppm: 1.35 (d, 6H, J=6 Hz; —CH(CH$_3$)$_2$), 1.62 (d, 3H, J=7 Hz; CH$_3$—), 3.50 (m, 1H, J=7 Hz; CH(CH$_3$)$_2$), 5.00 (q, 1H, J=7 Hz; —CO—CH—), 7.52 (d, 1H, J=2 Hz, H-thiophene) and 8.44 (d, 1H, J=2 Hz; H-thiophene).

EXAMPLE 8

4-[α-(sec-butylaminopropionyl)]-2-chlorothiophene hydrochloride

From 32.2 g of α-bromo-2-chloro-4-propionylthiophene in 40 ml of acetonitrile and 23.5 g of sec-butylamine, and operating as described in Ex. 1, 30 g of crude product are isolated, respective hydrochloride (20 g) formed in ethyl ether is recrystallized in isopropanol to give 6.55 g (21%) of a white solid, m.p. 206°-207° C. and analysis correct.

IR IR Spectrum (KBr) cm$^{-1}$: 3160–2400, 1680, 1550, 1420, 1210, 1195, 1105, 1005, 870, 805.

$^1$H—NMR Spectrum (CD$_2$OD) ppm: 1.00 (2t, 3H, J=7.0 Hz; CH$_3$—CH$_2$—), 1.38 (d, 3H, J=6.5 Hz; CH$_3$—CH—NH—), 1.63 (d+wide band, 5H, J=7 Hz; CH$_3$ and —CH$_2$), 3.14 (m, 1H; >CH—NH—), 5.12 (m, 1H; >CH—CO—), 7.53 (d, 1H, J=2 Hz; H-thiophene) and 8.60 (d, 1H, J=2 Hz; H-thiophene).

It will be understood that each of the elements described above, or two or more together, may also find a useful application in other types of compositions differing from the types described above.

While the invention has been illustrated and described as embodied in thiophene ring-substituted α-(alkylaminopropionyl)-thiophenes, process for the production thereof and pharmaceutical compositions containing the same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of the invention.

What is claimed as new and desired to be protected by Letters Patent is set forth in the appended claims.

We claim:

1. Thiophene ring-substituted α-(alkylaminopropionyl)thiophenes represented by the general formula (I):

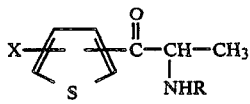

wherein X is methyl or chlorine,

R is alkyl, linear or branched, having 3 to 4 carbon atoms and pharmacologically-acceptable salts thereof.

2. Compound of claim 1 which is 2-[α-(sec-butylaminopropionyl)]-4-chlorothiophene and HCl.

3. Compound of claim 1 which is 2-[α-(sec-butylaminopropionyl)]-4-methylthiophene and HCl.

4. Compound of claim 1 which is 2-[α-(n-propylaminopropionyl)]-4-methylthiophene and HCl.

5. Compound of claim 1 which is 2-[α-(iso-propylaminopropionyl)]-5-chlorothiophene and HCl.

6. Compound of claim 1 which is 2-[α-(n-propylaminopropionyl)]-5-chlorothiophene and HCl.

7. Compound of claim 1 which is 2-[α-(sec-butylaminopropionyl)]-5-chlorothiophene and HCl.

8. Compound of claim 1 which is 4-[α-(iso-propylaminopropionyl)]-2-chlorothiophene and HCl.

9. Compound of claim 1 which is 4-[α-(sec-butylaminopropionyl)]-2-chlorothiophene and HCl.

10. Pharmaceutical compositions useful for the treatment of depressive diseases comprising an effective amount of one or more compounds as claimed in claim 1 together with a pharmaceutically-acceptable carrier.

11. Method for the treatment of depressive diseases in a subject in need for the same, comprising the step of administering an effective antidepressant agent of claim 1 to said patient.

* * * * *